US008637637B2

(12) United States Patent
Sun et al.

(10) Patent No.: US 8,637,637 B2
(45) Date of Patent: Jan. 28, 2014

(54) FC FUSION PROTEINS OF HUMAN GROWTH HORMONE

(76) Inventors: Bill Nai-Chau Sun, Shanghai (CN); Ruey-shyan Liou, Sugar Land, TX (US); Cecily Rou-Yun Sun, Shanghai (CN); Lee-Hwei King Sun, Houston, TX (US)

( * ) Notice: Subject to any disclaimer, the term of this patent is extended or adjusted under 35 U.S.C. 154(b) by 0 days.

(21) Appl. No.: 12/657,004

(22) Filed: Jan. 12, 2010

(65) Prior Publication Data

US 2012/0116056 A1 May 10, 2012

(51) Int. Cl.
*C07K 17/00* (2006.01)

(52) U.S. Cl.
USPC .......... 530/350

(58) Field of Classification Search
None
See application file for complete search history.

(56) References Cited

U.S. PATENT DOCUMENTS

| | | | | |
|---|---|---|---|---|
| 5,116,964 | A | 5/1992 | Capon et al. | |
| 5,349,053 | A | 9/1994 | Landolfi | |
| 5,541,087 | A | 7/1996 | Lo et al. | |
| 6,500,448 | B1 * | 12/2002 | Johnson et al. | 424/423 |
| 6,566,328 | B1 | 5/2003 | Rosen et al. | |
| 6,797,493 | B2 | 9/2004 | Sun et al. | |
| 6,900,292 | B2 | 5/2005 | Sun et al. | |
| 7,122,515 | B2 * | 10/2006 | Johannsson et al. | 514/7.4 |
| 2006/0094083 | A1 * | 5/2006 | Choi et al. | 435/69.4 |
| 2011/0293554 | A1 * | 12/2011 | Yan et al. | 424/85.1 |

OTHER PUBLICATIONS

Isaksson OG, et al (1985) “Mode of action of pituitary growth hormone on target cells” Annu. Rev. Physiol. 47:483-499.
Carter-Su C., et al (1996) “Molecular Mechanism of Growth Hormone Action” Annu. Rev. Physiol. 58: 187-207.
Billestrup N. et al (1998) “Molecular Mechanism of Growth Hormone Signaling” Endocrine Journal 45(Suppl) S41-S45.
Ashkenazi A and Chamow SM (1997) “Immunoadhesins as research tools and therapeutic agents” Curr. Opin. Immunol, 9: 195-200.
Jefferis et al (1998) “IgG-Fc-mediated effector definition of interaction sites for effector functions: molecular definition of interaction sites . . . ” Immunol. Rev. 163:59-76.
Armour K. et al (1999) “Recombinant Human IgG Molecules lacking Fc gamma Receptor I Binding and Monocyte Triggering . . . ” Eur. J. Immunol. 29:2613-2624, 1998.
Duncan A. and Winter G. (1988) “The Binding Site for C1q on IgG” Nature 332: 738-740.

* cited by examiner

*Primary Examiner* — Nashaat Nashed

(57) ABSTRACT

Fc fusion proteins of human growth hormone with good biological activities relative to rhGH on a molar basis are disclosed. The hGH-L-vFc fusion protein comprises hGH, a flexible peptide linker of about 20 or fewer amino acids, and a human IgG Fc variant. The Fc variant is of a non-lytic nature and shows minimal undesirable Fc-mediated side effects. A method is also disclosed to make or produce such fusion proteins at high expression levels. Such hGH-L-vFc fusion proteins exhibit extended or prolonged serum half-life and/or good biological activities relative to that of rhGH on a molar basis, leading to improved pharmacokinetics and pharmacodynamics, thus fewer injections will be needed within a period of time.

4 Claims, 4 Drawing Sheets

Figure 1. Amino acid sequence alignment in human IgG isotypes and their variants.

| Human IgG Isotype | Amino Acid Position |
|---|---|
| | 228……234 235 236 237……330 331 |
| G1 | Pro…….Leu Leu Gly Gly……Ala Pro |
| G2 | Pro…….Val Ala …. Gly……Ala Pro |
| G4 | Ser…….Phe Leu Gly Gly……Ser Ser |
| G1 variant | Pro…….***Val*** ***Ala*** Gly Gly……Ala ***Ser*** |
| G2 variant | Pro…….Val Ala …. Gly……Ala ***Ser*** |
| G4 variant | ***Pro***…….Phe ***Ala*** Gly Gly……..Ser Ser |

| ID number | Corresponding Row in this Figure 1 |
|---|---|
| SEQ ID NO:22 | G1 variant |
| SEQ ID NO:18 | G2 variant |
| SEQ ID NO:20 | G4 variant |

Figure 2A. DNA and deduced amino acid sequences of hGH-L-vFc$_{\gamma 2}$

```
aag ctt cta gct gca atg gct aca ggc tcc cgg acg tcc ctg ctc ctg gct ttt ggc ctg   60
HindIII              M   A   T   G   S   R   T   S   L   L   L   A   F   G   L
                    -26                     -20
ctc tgc ctg ccc tgg ctt caa gag ggc agt gcc ttc cca acc att ccc tta tcc agg ctt  120
 L   C   L   P   W   L   Q   E   G   S   A   F   P   T   I   P   L   S   R   L
    -10                                 -1   1
ttt gac aac gct atg ctc cgc gcc cat cgt ctg cac cag ctg gcc ttt gac acc tac cag  180
 F   D   N   A   M   L   R   A   H   R   L   H   Q   L   A   F   D   T   Y   Q
10                                      20
gag ttt gaa gaa gcc tat atc cca aag gaa cag aag tat tca ttc ctg cag aac ccc cag  240
 E   F   E   E   A   Y   I   P   K   E   Q   K   Y   S   F   L   Q   N   P   Q
30                                      40
acc tcc ctc tgt ttc tca gag tct att ccg aca ccc tcc aac agg gag gaa aca caa cag  300
 T   S   L   C   F   S   E   S   I   P   T   P   S   N   R   E   E   T   Q   Q
50                                      60
aaa tcc aac cta gag ctg ctc cgc atc tcc ctg ctg ctc atc cag tcg tgg ctg gag ccc  360
 K   S   N   L   E   L   L   R   I   S   L   L   L   I   Q   S   W   L   E   P
70                                      80
gtg cag ttc ctc agg agt gtc ttc gcc aac agc ctg gtg tac ggc gcc tct gac agc aac  420
 V   Q   F   L   R   S   V   F   A   N   S   L   V   Y   G   A   S   D   S   N
90                                      100
gtc tat gac ctc cta aag gac cta gag gaa ggc atc caa acg ctg atg ggg agg ctg gaa  480
 V   Y   D   L   L   K   D   L   E   E   G   I   Q   T   L   M   G   R   L   E
110                                     120
gat ggc agc ccc cgg act ggg cag atc ttc aag cag acc tac agc aag ttc gac aca aac  540
 D   G   S   P   R   T   G   Q   I   F   K   Q   T   Y   S   K   F   D   T   N
130                                     140
tca cac aac gat gac gca cta ctc aag aac tac ggg ctg ctc tac tgc ttc agg aag gac  600
 S   H   N   D   D   A   L   L   K   N   Y   G   L   L   Y   C   F   R   K   D
150                                     160
atg gac aag gtc gag aca ttc ctg cgc atc gtg cag tgc cgc tct gtg gag ggc agc tgt  660
 M   D   K   V   E   T   F   L   R   I   V   Q   C   R   S   V   E   G   S   C
170                                     180
ggc ttc gga tcc ggt ggc ggt tcc ggt gga ggc gga agc ggc ggt gga gga tca gtc gag  720
 G   F   G   S   G   G   G   S   G   G   G   G   S   G   G   G   G   S   V   E
190                                     200
tgc cca ccg tgc cca gca cca cct gtg gca gga ccg tca gtc ttc ctc ttc ccc cca aaa  780
 C   P   P   C   P   A   P   P   V   A   G   P   S   V   F   L   F   P   P   K
210                                     220
ccc aag gac acc ctc atg atc tcc cgg acc cct gag gtc acg tgc gtg gtg gtg gac gtg  840
 P   K   D   T   L   M   I   S   R   T   P   E   V   T   C   V   V   V   D   V
230                                     240
agc cac gaa gac ccc gag gtc cag ttc aac tgg tac gtg gac ggc gtg gag gtg cat aat  900
 S   H   E   D   P   E   V   Q   F   N   W   Y   V   D   G   V   E   V   H   N
250                                     260
gcc aag aca aag cca cgg gag gag cag ttc aac agc acg ttc cgt gtg gtc agc gtc ctc  960
 A   K   T   K   P   R   E   E   Q   F   N   S   T   F   R   V   V   S   V   L
270                                     280
acc gtt gtg cac cag gac tgg ctg aac ggc aag gag tac aag tgc aag gtc tcc aac aaa 1020
 T   V   V   H   Q   D   W   L   N   G   K   E   Y   K   C   K   V   S   N   K
290                                     300
ggc ctc cca gcc tcc atc gag aaa acc atc tcc aaa acc aaa ggg cag ccc cga gaa cca 1080
 G   L   P   A   S   I   E   K   T   I   S   K   T   K   G   Q   P   R   E   P
310                                     320
cag gtg tac acc ctg ccc cca tcc cgg gag gag atg acc aag aac cag gtc agc ctg acc 1140
 Q   V   Y   T   L   P   P   S   R   E   E   M   T   K   N   Q   V   S   L   T
330                                     340
tgc ctg gtc aaa ggc ttc tac ccc agc gac atc gcc gtg gag tgg gag agc aat ggg cag 1200
 C   L   V   K   G   F   Y   P   S   D   I   A   V   E   W   E   S   N   G   Q
350                                     360
ccg gag aac aac tac aag acc aca cct ccc atg ctg gac tcc gac ggc tcc ttc ttc ctc 1260
 P   E   N   N   Y   K   T   T   P   P   M   L   D   S   D   G   S   F   F   L
370                                     380
tac agc aag ctc acc gtg gac aag agc agg tgg cag cag ggg aac gtc ttc tca tgc tcc 1320
 Y   S   K   L   T   V   D   K   S   R   W   Q   Q   G   N   V   F   S   C   S
390                                     400
gtg atg cat gag gct ctg cac aac cac tac acg cag aag agc ctc tcc ctg tct ccg ggt 1380
 V   M   H   E   A   L   H   N   H   Y   T   Q   K   S   L   S   L   S   P   G
410                                     420
aaa tga gaa ttc                                                                 1392
 K       EcoRI
430
```

Figure 2B. DNA and deduced amino acid sequences of hGH-L-vFc$_{\gamma 4}$

```
aag ctt cta gct gca atg gct aca ggc tcc cgg acg tcc ctg ctc ctg gct ttt ggc ctg    60
HindIII             M   A   T   G   S   R   T   S   L   L   L   A   F   G   L
                   -26                     -20
ctc tgc ctg ccc tgg ctt caa gag ggc agt gcc ttc cca acc att ccc tta tcc agg ctt   120
 L   C   L   P   W   L   Q   E   G   S   A   F   P   T   I   P   L   S   R   L
    -10                                 -1   1
ttt gac aac gct atg ctc cgc gcc cat cgt ctg cac cag ctg gcc ttt gac acc tac cag   180
 F   D   N   A   M   L   R   A   H   R   L   H   Q   L   A   F   D   T   Y   Q
10                                      20
gag ttt gaa gaa gcc tat atc cca aag gaa cag aag tat tca ttc ctg cag aac ccc cag   240
 E   F   E   E   A   Y   I   P   K   E   Q   K   Y   S   F   L   Q   N   P   Q
30                                      40
acc tcc ctc tgt ttc tca gag tct att ccg aca ccc tcc aac agg gag gaa aca caa cag   300
 T   S   L   C   F   S   E   S   I   P   T   P   S   N   R   E   E   T   Q   Q
50                                      60
aaa tcc aac cta gag ctg ctc cgc atc tcc ctg ctg ctc atc cag tcg tgg ctg gag ccc   360
 K   S   N   L   E   L   L   R   I   S   L   L   L   I   Q   S   W   L   E   P
70                                      80
gtg cag ttc ctc agg agt gtc ttc gcc aac agc ctg gtg tac ggc gcc tct gac agc aac   420
 V   Q   F   L   R   S   V   F   A   N   S   L   V   Y   G   A   S   D   S   N
90                                      100
gtc tat gac ctc cta aag gac cta gag gaa ggc atc caa acg ctg atg ggg agg ctg gaa   480
 V   Y   D   L   L   K   D   L   E   E   G   I   Q   T   L   M   G   R   L   E
110                                     120
gat ggc agc ccc cgg act ggg cag atc ttc aag cag acc tac agc aag ttc gac aca aac   540
 D   G   S   P   R   T   G   Q   I   F   K   Q   T   Y   S   K   F   D   T   N
130                                     140
tca cac aac gat gac gca cta ctc aag aac tac ggg ctg ctc tac tgc ttc agg aag gac   600
 S   H   N   D   D   A   L   L   K   N   Y   G   L   L   Y   C   F   R   K   D
150                                     160
atg gac aag gtc gag aca ttc ctg cgc atc gtg cag tgc cgc tct gtg gag ggc agc tgt   660
 M   D   K   V   E   T   F   L   R   I   V   Q   C   R   S   V   E   G   S   C
170                                     180
ggc ttc gga tcc ggt ggc ggt tcc ggt gga ggc gga agc ggc ggt gga gga tca gag tcc   720
 G   F   G   S   G   G   G   S   G   G   G   G   S   G   G   G   G   S   E   S
190                                     200
aaa tat ggt ccc cca tgc cca cca tgc cca gca cct gag ttc gcg ggg gga cca tca gtc   780
 K   Y   G   P   P   C   P   P   C   P   A   P   E   F   A   G   G   P   S   V
210                                     220
ttc ctg ttc ccc cca aaa ccc aag gac act ctc atg atc tcc cgg acc cct gag gtc acg   840
 F   L   F   P   P   K   P   K   D   T   L   M   I   S   R   T   P   E   V   T
230                                     240
tgc gtg gtg gtg gac gtg agc cag gaa gac ccc gag gtc cag ttc aac tgg tac gtg gat   900
 C   V   V   V   D   V   S   Q   E   D   P   E   V   Q   F   N   W   Y   V   D
250                                     260
ggc gtg gag gtg cat aat gcc aag aca aag ccg cgg gag gag cag ttc aac agc acg tac   960
 G   V   E   V   H   N   A   K   T   K   P   R   E   E   Q   F   N   S   T   Y
270                                     280
cgt gtg gtc agc gtc ctc acc gtc ctg cac cag gac tgg ctg aac ggc aag gag tac aag  1020
 R   V   V   S   V   L   T   V   L   H   Q   D   W   L   N   G   K   E   Y   K
290                                     300
tgc aag gtc tcc aac aaa ggc ctc ccg tcc tcc atc gag aaa acc atc tcc aaa gcc aaa  1080
 C   K   V   S   N   K   G   L   P   S   S   I   E   K   T   I   S   K   A   K
310                                     320
ggg cag ccc cga gag cca cag gtg tac acc ctg ccc cca tcc cag gag gag atg acc aag  1140
 G   Q   P   R   E   P   Q   V   Y   T   L   P   P   S   Q   E   E   M   T   K
330                                     340
aac cag gtc agc ctg acc tgc ctg gtc aaa ggc ttc tac ccc agc gac atc gcc gtg gag  1200
 N   Q   V   S   L   T   C   L   V   K   G   F   Y   P   S   D   I   A   V   E
350                                     360
tgg gag agc aat ggg cag ccg gag aac aac tac aag acc acg cct ccc gtg ctg gac tcc  1260
 W   E   S   N   G   Q   P   E   N   N   Y   K   T   T   P   P   V   L   D   S
370                                     380
gac ggc tcc ttc ttc ctc tac agc agg cta acc gtg gac aag agc agg tgg cag gag ggg  1320
 D   G   S   F   F   L   Y   S   R   L   T   V   D   K   S   R   W   Q   E   G
390                                     400
aat gtc ttc tca tgc tcc gtg atg cat gag gct ctg cac aac cac tac aca cag aag agc  1380
 N   V   F   S   C   S   V   M   H   E   A   L   H   N   H   Y   T   Q   K   S
410                                     420
ctc tcc ctg tct ctg ggt aaa tga gaa ttc                                          1410
 L   S   L   S   L   G   K      EcoRI
430
```

Figure 2C. DNA and deduced amino acid sequences of hGH-L-vFc$_{\gamma1}$

```
aag ctt cta gct gca atg gct aca ggc tcc cgg acg tcc ctg ctc ctg gct ttt ggc ctg   60
HindIII             M   A   T   G   S   R   T   S   L   L   A   F   G   L
                   -26                     -20
ctc tgc ctg ccc tgg ctt caa gag ggc agt gcc ttc cca acc att ccc tta tcc agg ctt  120
 L   C   L   P   W   L   Q   E   G   S   A   F   P   T   I   P   L   S   R   L
   -10                                  -1   1
ttt gac aac gct atg ctc cgc gcc cat cgt ctg cac cag ctg gcc ttt gac acc tac cag  180
 F   D   N   A   M   L   R   A   H   R   L   H   Q   L   A   F   D   T   Y   Q
10                                      20
gag ttt gaa gaa gcc tat atc cca aag gaa cag aag tat tca ttc ctg cag aac ccc cag  240
 E   F   E   E   A   Y   I   P   K   E   Q   K   Y   S   F   L   Q   N   P   Q
30                                      40
acc tcc ctc tgt ttc tca gag tct att ccg aca ccc tcc aac agg gag gaa aca caa cag  300
 T   S   L   C   F   S   E   S   I   P   T   P   S   N   R   E   E   T   Q   Q
50                                      60
aaa tcc aac cta gag ctg ctc cgc atc tcc ctg ctg ctc atc cag tcg tgg ctg gag ccc  360
 K   S   N   L   E   L   L   R   I   S   L   L   L   I   Q   S   W   L   E   P
70                                      80
gtg cag ttc ctc agg agt gtc ttc gcc aac agc ctg gtg tac ggc gcc tct gac agc aac  420
 V   Q   F   L   R   S   V   F   A   N   S   L   V   Y   G   A   S   D   S   N
90                                      100
gtc tat gac ctc cta aag gac cta gag gaa ggc atc caa acg ctg atg ggg agg ctg gaa  480
 V   Y   D   L   L   K   D   L   E   E   G   I   Q   T   L   M   G   R   L   E
110                                     120
gat ggc agc ccc cgg act ggg cag atc ttc aag cag acc tac agc aag ttc gac aca aac  540
 D   G   S   P   R   T   G   Q   I   F   K   Q   T   Y   S   K   F   D   T   N
130                                     140
tca cac aac gat gac gca cta ctc aag aac tac ggg ctg ctc tac tgc ttc agg aag gac  600
 S   H   N   D   D   A   L   L   K   N   Y   G   L   L   Y   C   F   R   K   D
150                                     160
atg gac aag gtc gag aca ttc ctg cgc atc gtg cag tgc cgc tct gtg gag ggc agc tgt  660
 M   D   K   V   E   T   F   L   R   I   V   Q   C   R   S   V   E   G   S   C
170                                     180
ggc ttc gga tcc ggt ggc ggt tcc ggt gga ggc gga agc ggc ggt gga gga tca gac aaa  720
 G   F   G   S   G   G   G   S   G   G   G   G   S   G   G   G   G   S   D   K
190                                     200
act cac aca tgc cca ccg tgc cca gca cct gaa gtc gcg ggg gga ccg tca gtc ttc ctc  780
 T   H   T   C   P   P   C   P   A   P   E   V   A   G   G   P   S   V   F   L
210                                     220
ttc ccc cca aaa ccc aag gac acc ctc atg atc tcc cgg aca cct gag gtc aca tgc gtg  840
 F   P   P   K   P   K   D   T   L   M   I   S   R   T   P   E   V   T   C   V
230                                     240
gtg gtg gac gtg agc cac gaa gac cct gag gtc aag ttc aac tgg tac gtg gac ggc gtg  900
 V   V   D   V   S   H   E   D   P   E   V   K   F   N   W   Y   V   D   G   V
250                                     260
gag gtg cat aat gcc aag aca aag ccg cgg gag gag cag tac aac agc acg tac cgg gtg  960
 E   V   H   N   A   K   T   K   P   R   E   E   Q   Y   N   S   T   Y   R   V
270                                     280
gtc agc gtc ctc acc gtc ctg cac cag gac tgg ctg aat ggc aag gag tac aag tgc aag 1020
 V   S   V   L   T   V   L   H   Q   D   W   L   N   G   K   E   Y   K   C   K
290                                     300
gtc tcc aac aaa gcc ctc cca gcc tcc atc gag aaa acc atc tcc aaa gcc aaa ggg cag 1080
 V   S   N   K   A   L   P   A   S   I   E   K   T   I   S   K   A   K   G   Q
310                                     320
ccc cga gaa cca cag gtg tac acc ctg ccc cca tcc cgg gat gag ctg acc aag aac cag 1140
 P   R   E   P   Q   V   Y   T   L   P   P   S   R   D   E   L   T   K   N   Q
330                                     340
gtc agc ctg acc tgc ctg gtc aaa ggc ttc tat ccc agc gac atc gcc gtg gag tgg gag 1200
 V   S   L   T   C   L   V   K   G   F   Y   P   S   D   I   A   V   E   W   E
350                                     360
agc aat ggg cag ccg gag aac aac tac aag acc acg cct ccc gtg ctg gac tcc gac ggc 1260
 S   N   G   Q   P   E   N   N   Y   K   T   T   P   P   V   L   D   S   D   G
370                                     380
tcc ttc ttc ctc tac agc aag ctc acc gtg gac aag agc agg tgg cag cag ggg aac gtc 1320
 S   F   F   L   Y   S   K   L   T   V   D   K   S   R   W   Q   Q   G   N   V
390                                     400
ttc tca tgc tcc gtg atg cat gag gct ctg cac aac cac tac acg cag aag agc ctc tcc 1380
 F   S   C   S   V   M   H   E   A   L   H   N   H   Y   T   Q   K   S   L   S
410                                     420
ctg tct ccg ggt aaa tga gaa ttc
1404
 L   S   P   G   K       EcoRI
430
```

FC FUSION PROTEINS OF HUMAN GROWTH HORMONE

BACKGROUND

Human growth hormone ("hGH") is produced in and released from the pituitary gland. The 22-kDa peptide hormone participates in much of the regulation of normal human growth and development. This pituitary hormone exhibits a multitude of biological effects, including linear growth (somatogenesis), lactation, activation of macrophages, and insulin-like effects, among others. These biological effects are mediated by the interaction between hGH and specific hGH Receptors (hGHR) on the surface of target cells through a cascade of biochemical events (see, for example, Isaksson et al., *Annu. Rev. Physiol.* 47:483-499, 1985; Friedrichsen et al., *Mol. Endocrino.* 15:136-148, 2001; Herrington et al., *Trends Endocrinol Metab.* 12:252-257, 2001).

Recombinant human Growth Hormone (rhGH) is used to treat growth failure due to deficiency of endogenous hGH secretion. Both children and adult patients with hGH deficiency have been treated successfully with rhGH. Other treatment applications for conditions that may involve short stature are in patients for Turner syndrome, chronic renal failure, Prader-Willi syndrome, and idiopathic short stature.

Supplemental hGH is a desirable treatment in cases of growth hormone deficiency for both children and adults. The half-life for the serum clearance of intravenous (i.v.) rhGH in healthy adults is approximately 20 min. The peak serum concentration for subcutaneous (s.c.) rhGH occurs in several hours after injection with an elimination half-life of 3 to 8 h. Treatment with hGH requires s.c. injection three times a week, or once daily to maintain suitable serum levels of hGH. For patients chronically receiving hGH, the frequent injections often result in patient compliance problems. From 1999 to 2004, a sustained-release form of rhGH (Nutropin Depot by Genentech and Alkermes) was in the market, allowing for fewer injections every 2 or 4 weeks instead of daily. The product was withdrawn due to high manufacturing costs. Several versions of PEGylated hGH (see, for example, Cox et al., *Endocrinol.* 148:1590-1597, 2007; Webster et al., *Xenobiotica.* 38: 1340-1351, 2008) have been reported to show longer half-life than rhGH yet often at the expense of bioactivities as a result of the PEGylation of the protein. It is therefore desirable to have a long-acting hGH with high activity that can be produced at a reasonable cost.

Immunoglobulins of IgG class are among the most abundant proteins in human blood. Their circulation half-lives can reach as long as 21 days. Fusion proteins have been reported to combine the Fc regions of IgG with the domains of another protein, such as various cytokines and soluble receptors (see, for example, Capon et al., *Nature* 337:525-531, 1989; Chamow et al., *Trends Biotechnol.* 14:52-60 (1996); U.S. Pat. Nos. 5,116,964 and 5,541,087). The prototype fusion protein is a homodimeric protein linked through cysteine residues in the hinge region of IgG Fc, resulting in a molecule similar to an IgG molecule without the CH1 domains and light chains. Due to the structural homology, Fc fusion proteins exhibit in vivo pharmacokinetic profile comparable to that of human IgG with a similar isotype. This approach has been applied to several therapeutically important cytokines, such as EPO, and G-CSF and soluble receptors, such as TNF-Rc and IL-5—Rc (see, for example, U.S. Pat. Nos. 5,349,053 and 6,224,867). To extend the circulating half-life of hGH and/or to increase its biological activity, it is desirable to make fusion proteins containing hGH linked to the Fc portion of the human IgG protein as disclosed or described in this invention.

In most of the reported Fc fusion protein molecules, a hinge region serves as a spacer between the Fc region and the cytokine or soluble receptor at the amino-terminus, allowing these two parts of the molecule to function separately (see, for example, Ashkenazi et al., *Current Opinion in Immunology,* 9:195-200, 1997). It is desirable that a human GH (rHG) fusion protein with an appropriate peptide linker between the hGH and Fc moieties (hGH-L-Fc) may be as good as or more active than rhGH, with in vitro activity similar to, better than, or preferably at least 2-fold as that of rhGH on a molar basis. It is discovered according to this invention that an added peptide linker present between hGH and a human IgG Fc variant may enhance the in vitro biological activity of the hGH-L-Fc molecule in two ways: (1) keeping the Fc region away from the hGHR binding sites on hGH, and (2) keeping one hGH from the other hGH molecule, so both hGH molecules can interact with hGHR on cell surface independently. For the present invention, a flexible peptide linker of about 20 or fewer amino acids in length is preferred. It is also desirable and more preferable to use a peptide linker comprising of two or more of the following amino acids: glycine, serine, alanine, and threonine.

The Fc region of human immunoglobulins plays a significant role in immune defense for the elimination of pathogens. Effector functions of IgG are mediated by the Fc region through two major mechanisms: (1) binding to the cell surface Fc receptors ($Fc_\gamma Rs$) can lead to ingestion of pathogens by phagocytosis or lysis by killer cells via the antibody-dependent cellular cytotoxicity (ADCC) pathway, or (2) binding to the C1q part of the first complement component C1 initiates the complement-dependent cytotoxicity (CDC) pathway, resulting in the lysis of pathogens. Among the four human IgG isotypes, IgG1 and IgG3 are effective in binding to $Fc_\gamma R$. The binding affinity of IgG4 to $Fc_\gamma R$ is an order of magnitude lower than that of IgG1 or IgG3, while binding of IgG2 to $Fc_\gamma R$ is below detection. Human IgG1 and IgG3 are also effective in binding to C1q and activating the complement cascade. Human IgG2 fixes complement poorly, and IgG4 appears quite deficient in the ability to activate the complement cascade (see, for example, Jefferis et al., *Immunol. Rev.* 163:59-76, 1998). For therapeutic use in humans, it is essential that when hGH-L-Fc binds to receptors on the cell surface of target cells, the Fc region of the fusion protein will not mediate undesirable effector functions, leading to the lysis or removal of these cells. Accordingly, the Fc region of hGH-L-Fc must be of a non-lytic nature, i.e. the Fc region must be inert in terms of binding to $Fc_\gamma Rs$ and C1q for the triggering of effector functions. It is clear that none of the naturally occurring IgG isotypes is suitable for use to produce the hGH-L-Fc fusion protein. To obtain a non-lytic Fc, certain amino acids of the natural Fc region have to be mutated for the attenuation of the effector functions.

By comparing amino acid sequences of human and murine IgG isotypes, a portion of Fc near the N-terminal end of the CH2 domain is implicated to play a role in the binding of IgG Fc to $Fc_\gamma Rs$. The importance of a motif at positions 234 to 237 has been demonstrated using genetically engineered antibodies (see, for example, Duncan et al., *Nature* 332:563-564, 1988). The numbering of the amino acid residues is according to the EU index as described in Kabat et al. (in *Sequences of Proteins of Immunological Interest,* 5th Edition, United States Department of Health and Human Services, 1991). Among the four human IgG isotypes, IgG1 and IgG3 bind $Fc_\gamma Rs$ the best and share the sequence Leu234-Leu-Gly-Gly237 (only IgG1 is shown in FIG. 1). In IgG4, which binds $Fc_\gamma Rs$ with a lower affinity, this sequence contains a single amino acid substitution, Phe for Leu at position 234. In IgG2, which does not bind $Fc_{\gamma}$Rs, there are two substitutions and a deletion leading to Val234-Ala-Gly237 (FIG. 1). To minimize the binding of Fc to $Fc_{\gamma}$R and hence the ADCC activity, Leu235 in IgG4 has been replaced by Ala (see, for example, Hutchins et al., *Proc. Natl. Acad. Sci. USA* 92:11980-11984, 1995). IgG1 has been altered in this motif by replacing Glu233-Leu-Leu235 with Pro233-Val-Ala235, which is the sequence from IgG2. This substitution resulted in an IgG1 variant devoid of $Fc_{\gamma}$R-mediated ability to deplete target cells in mice (see, for example, Isaacs et al., *J. Immunol.* 161: 3862-3869, 1998).

A second portion that appears to be important for both $Fc_{\gamma}$R and C1q binding is located near the carboxyl-terminal end of CH2 domain of human IgG (see, for example, Duncan et al., *Nature* 332:738-740, 1988). Among the four human IgG isotypes, there is only one site within this portion that shows substitutions: Ser330 and Ser331 in IgG4 replacing Ala330 and Pro331 present in IgG1, IgG2, and IgG3 (FIG. 1). The presence of Ser330 does not affect the binding to $Fc_{\gamma}$R or C1q. The replacement of Pro331 in IgG1 by Ser virtually abolished IgG1 ability to C1q binding, while the replacement of Ser331 by Pro partially restored the complement fixation activity of IgG4 (see, for example, Tao et al., *J. Exp. Med.* 178:661-667, 1993; Xu et al., *J. Biol. Chem.* 269:3469-3474, 1994).

We discover that at least three Fc variants (vFc) can be designed for the production of hGH-L-vFc fusion proteins (FIG. 1). Human IgG2 Fc does not bind $Fc_{\gamma}$R but showed weak complement activity. An $Fc_{\gamma 2}$ variant with Pro331Ser mutation should have less complement activity than natural $Fc_{\gamma 2}$ while remain nonbonding to $Fc_{\gamma}$R. IgG4 Fc is deficient in activating the complement cascade, and its binding affinity to $Fc_{\gamma}$R is about an order of magnitude lower than that of the most active isotype, IgG1. An $Fc_{\gamma 4}$ variant with Leu235Ala mutation should exhibit minimal effector functions as compared to the natural $Fc_{\gamma 4}$. The $Fc_{\gamma 1}$ variant with Leu234Val, Leu235Ala and Pro331Ser mutations also will exhibit much less effector functions than the natural $Fc_{\gamma 1}$. These Fc variants are more suitable for the preparation of the hGH fusion proteins than naturally occurring human IgG Fc. It is possible that other replacements can be introduced for the preparation of a non-lytic Fc without compromising the circulating half-life or causing any undesirable conformational changes.

There are many advantages with the present invention. The good activity and/or preferably prolonged presence of the hGH-L-vFc fusion protein in the serum can lead to lower dosages as well as less frequent injections. Less fluctuations of the drug in serum concentrations also means improved safety and tolerability. Less frequent injections may result in better patient compliance and quality of life. The hGH-L-vFc fusion protein containing a non-lytic Fc variant will therefore contribute significantly to the long term management of hGH deficiency in patients that may involve short stature and other conditions including Turner syndrome, chronic renal failure, Prader-Willi syndrome, and idiopathic short stature.

SUMMARY OF THE INVENTION

One aspect of the present invention relates to a hGH-L-vFc fusion protein. The hGH-L-vFc fusion protein comprises hGH, a peptide linker, and a human IgG Fc variant. It is preferable that the human IgG Fc variant comprises a hinge, a CH2 domain, and a CH3 domain selected from the group consisting of (A) human IgG1 with Leu234Val, Leu235Ala, and Pro331Ser mutations, (B) human IgG2 with Pro331Ser mutation, and (C) human IgG4 with Ser228Pro and Leu235Ala mutations. It is preferably to use a flexible peptide linker of 20 or fewer amino acids in length which comprises of two or more of the following amino acids: glycine, serine, alanine, and threonine. The IgG Fc variants are preferably of non-lytic nature and contain amino acid mutations as compared to naturally occurring IgG Fc. It is disclosed herein as an aspect of the present invention that the hGH-L-vFc fusion protein exhibits good in vitro biological activity relative to that of rhGH on a molar basis. Further, it is also an embodiment of the invention that the hGH-L-vFc fusion protein exhibits a plasma half-life that is comparable to or equal to, preferably longer than [i.e. prolonged], and more preferably at least 2 times as long as that of rhGH when administered in vivo.

It is another embodiment of the present invention that the human Ig Fc comprises a hinge, CH2 domain and CH3 domain of human IgG, such as human IgG1, IgG2, and IgG4. The CH2 domain contains amino acid mutations at positions 228, 234, 235, and 331 (defined by the EU numbering system) to attenuate the effector functions of Fc.

In yet another embodiment of the present invention, a method is disclosed to generate, make or produce such fusion proteins from a mammalian cell line such as a CHO-derived cell line. Growing transfected cell lines under conditions such that the recombinant fusion protein is expressed in its growth medium in excess of 10 μg, preferably 30 μg, per million cells in a 24 hour period. These hGH-L-vFc fusion proteins exhibit good biological activity and extended or prolonged serum half-life without undesirable side effects, leading to improved pharmacokinetics and pharmacodynamics, thus lower dosages and fewer injections would be needed to achieve similar efficacies. Another aspect of the invention involves a recombinant hGH-L-vFc fusion protein which exhibits a plasma half-life that is comparable to or equal to, preferably longer than, and more preferably at least 2 times as long as that of rhGH when administered in vivo. Further, the present invention discloses peptide linkers which contain about 20 or fewer amino acids are present between hGH and the human IgG Fc variant; and the peptide linker comprises two or more amino acids selected from the group consisting of glycine, serine, alanine, and threonine.

A further aspect of the present invention also involves a method for making a recombinant fusion protein comprising hGH, a flexible peptide linker, and a human IgG Fc variant, which method comprises: (a) generating a CHO-derived cell line; (b) growing the cell line under conditions the recombinant fusion protein is expressed in its growth medium in excess of 10 μg, more preferably 30 μg, per million cells in a 24 hour period; and (c) purifying the expressed protein from step (b), wherein the recombinant fusion protein exhibits a good in vitro biological activity on a molar basis relative to that of rhGH, and/or a preferably prolonged plasma half-life that is comparable to, or equal to, preferably longer than, and more preferably at least 2 times as long as that of rhGH when administered in vivo, or both, wherein the flexible peptide linker containing about 20 or fewer amino acids is present between hGH and the human IgG Fc variant; and the peptide linker comprises two or more amino acids selected from the group consisting of glycine, serine, alanine, and threonine; wherein the human IgG Fc variant comprises a hinge, CH2, and CH3 domains selected from the group consisting of human IgG2 with Pro331Ser mutation, human IgG4 with Ser228Pro and Leu235Ala mutations, and human IgG1 with Leu234Val, Leu235Ala, and Pro331Ser mutations.

A further aspect of the present invention relates to a CHO-derived cell line producing the hGH-L-vFc fusion protein as disclosed herein. The human IgG-Fc variant comprises a hinge, CH2, and CH3 domains of human IgG selected from the group consisting of IgG1, IgG2, and IgG4. The IgG Fc contains amino acid mutations to attenuate effector functions, and a flexible peptide linker containing about 20 or fewer amino acids is present between hGH and human IgG Fc variant. And the hGH-L-vFc fusion protein exhibits a good in vitro biological activity relative to that of rhGH on a molar basis. Another aspect also involves such a CHO-derived cell line producing the hGH-L-vFc fusion protein wherein the protein exhibits a plasma half-life that is comparable to or equal to, preferably longer than [i.e. prolonged], and more preferably at least 2 times as long as that of rhGH when administered in vivo.

BRIEF DESCRIPTIONS OF THE DRAWINGS

FIG. 1 shows the amino acid sequence alignment from the hinge and CH2 regions of human IgG1, IgG2, IgG4 and their variants. Three portions are compared: amino acid position 228, 234-237, and 330-331. Amino acid mutations of the variants are indicated in bold italics. The EU numbering system is used for the amino acid residues.

FIG. 2 shows the nucleotide sequence and deduced amino acid sequence of FIG. 2A . . . hGH-L-vFc$_{\gamma2}$ SEQ ID No. 17 and SEQ ID No. 18 FIG. 2B . . . hGH-L-vFc$_{\gamma4}$ SEQ ID No. 19 and SEQ ID No. 20 FIG. 2C . . . hGH-L-vFc$_{\gamma1}$ SEQ ID No. 21 and SEO ID No. 22 as the HindIII-EcoRI fragment in the respective pGFP expression vector. The peptide from amino acid residues −26 to −1 is the leader peptide of hGH. The mature protein contains hGH (amino acid residues 1 to 191), a peptide linker (amino acid residues 192 to 207), and a Fc variant (amino acid residues 208 to 430 of vFc$_{12}$, 208 to 436 of vFc$_{\gamma4}$, and 208 to 434 of vFc$_{\gamma1}$). In the Fc regions, nucleotide and corresponding amino acid mutations in bold are also underlined.

DETAILED DESCRIPTION OF THE INVENTION

1. Construction of the Gene Encoding the hGH-L-vFc$_{\gamma2}$/Fusion Protein

A fusion protein is assembled from several DNA segments. To obtain the gene encoding the leader peptide and mature protein of human GH, a synthetic gene is prepared to have the same sequence as human growth hormone 1 of NCBI Reference Sequence: NM_000515.3. Using the DNA sequence from 5'- to 3'-terminus of the hGH gene, four oligonucleotides, each of about 180 nucleotides in length containing overlapping sequences, are synthesized. Using these four synthetic oligonucleotides, DNA fragments of approximately 650-bp in length are assembled by PCR. For the convenience of cloning, SEQ ID NO:1 (Table 1), which incorporates a restriction enzyme cleavage site (HindIII) is used as the 5' oligonucleotide primer. Table 1 shows the sequences of oligonucleotides used for the cloning of the fusion proteins. The 3' primer (SEQ ID NO:2) incorporates another restriction enzyme cleavage site (BamHI site). The resulting DNA fragments of approximately 650 bp in length are inserted into a holding vector such as pUC19 at the HindIII and BamHI sites to give the phGH plasmid. The sequence of the hGH gene is confirmed by DNA sequencing.

The hinge domain of human IgG2 heavy chain contains 12 amino acid residues (GluArgLysCysCysValGluCysProProCysPro) including 4 cysteine residues. Out of these 4 cysteine residues, the 3$^{rd}$ and 4$^{th}$ are involved in the formation of disulfide bonding between two heavy chains. The 1$^{st}$ and 2$^{nd}$ cysteine residues are deleted to avoid nonspecific disulfide bonding. The hinge domain of Fc$_{\gamma2}$ can be truncated to contain 7 amino acids (ValGluCysProProCysPro). The gene encoding the Fc region of human IgG2 (Fc$_{\gamma2}$) is obtained by reverse transcription and PCR using RNA prepared from human leukocytes and appropriate 5' (SEQ ID NO:3) and 3' (SEQ ID NO:4) primers. Resulting DNA fragments of Fc$_{\gamma2}$ containing complete sequences of the truncated hinge, CH2 and CH3 domains of IgG2 will be used as the template to generate the Fc$_{\gamma2}$ Pro331Ser variant (vFc$_{72}$) in which Pro at position 331 of Fc$_{\gamma2}$ is replaced with Ser. To incorporate this mutation, two segments are produced and then assembled by using the natural Fc$_{\gamma2}$ as the template in overlapping PCR. The 5' segment is generated by using SEQ ID NO:3 as the 5' primer and SEQ ID NO:5 as the 3' primer. The 3' segment is generated by using SEQ ID NO:6 as the 5' primer and SEQ ID NO:4 as the 3' primer. These two segments are then joined at the region covering the Pro331Ser mutation by using SEQ ID NO:7 as the 5' primer and SEQ ID NO:4 as the 3' primer. The SEQ ID NO:7 primer contains sequences encoding a 16-amino acid Gly-Ser peptide linker including a BamHI restriction enzyme site. The resulting DNA fragments of approximately 700 bp in length are inserted into a holding vector such as pUC19 at the BamHI and EcoRI sites to give the pL-vFcγ2 plasmid. The sequence of the gene is confirmed by DNA sequencing.

To prepare the hGH-L-vFc$_{\gamma2}$ fusion gene, the hGH fragment is excised from the phGH plasmid with HindIII and BamHI and is purified by agarose gel electrophoresis. The purified fragment is then inserted to the 5'-end of the peptide linker in the pL-vFcγ2 plasmid to give the phGH-L-vFcγ2 plasmid. The fusion gene comprises hGH, a Gly-Ser peptide linker and the Fc$_{\gamma2}$ variant gene.

The presence of a peptide linker between the hGH and Fc moieties may increase the flexibility of hGH and enhance its biological activity (see, for example, U.S. Pat. Nos. 6,797,493 and 6,900,292). For the present invention, a peptide linker of about 20 or fewer amino acids in length is preferred. Peptide linker comprising two or more of the following amino acids: glycine, serine, alanine, and threonine can be used. An example of the peptide linker contains Gly-Ser peptide building blocks, such as GlyGlyGlyGlySer. FIG. 2A shows a fusion gene containing sequences encoding hGH, a 16-amino acid peptide linker (GlySerGlyGlyGlySerGlyGlyGlyGlySerGlyGlyGlyGlySer), and the Fc$_{\gamma2}$ Pro331 Ser variant.

The complete gene encoding the hGH-L-vFc$_{\gamma2}$ fusion protein is then inserted at the HindIII and EcoRI sites of a mammalian expression vector, such as pcDNA3 (Invitrogen). The final expression vector plasmid, named pGFP2, contains the cytomegalovirus early gene promoter-enhancer which is required for high level expression in mammalian cells. The plasmid also contains selectable markers to confer ampicillin resistance in bacteria, and G418 resistance in mammalian cells. In addition, the pGFP2 expression vector contains the dihydrofolate reductase (DHFR) gene to enable the co-amplification of the hGH-L-vFc$_{\gamma2}$ fusion gene and the DHFR gene in the presence of methotrexate (MTX) when the host cells are deficient in the DHFR gene expression (see, for example, U.S. Pat. No. 4,399,216).

2. Construction of the Gene Encoding the hGH-L-vFc$_{\gamma4}$ Fusion Protein

Human IgG4 is observed partly as half antibody molecules due to the dissociation of the inter-heavy chain disulfide bonds in the hinge domain. This is not seen in the other three human IgG isotypes. A single amino acid substitution replacing Ser228 with Pro, which is the residue found at this position in IgG2 and IgG4, leads to the formation of IgG4 complete antibody molecules (see, for example, Angal et al., *Molec. Immunol.* 30:105-108, 1993; Owens et al., *Immunotechnology* 3:107-116, 1997; U.S. Pat. No. 6,204,007). The Fc$_{\gamma4}$variant containing Leu235Ala mutation for the attenuation of FcR binding will also give rise to a homogeneous fusion protein preparation with this additional Ser228Pro mutation.

The gene encoding the Fc region of human IgG4 ($Fc_{\gamma 4}$) is obtained by reverse transcription and PCR using RNA prepared from human leukocytes and appropriate 5' primer (SEQ ID NO:8) and 3' primer (SEQ ID NO:9). Resulting DNA fragments of $Fc_{\gamma 4}$containing complete sequences of the hinge, CH2 and CH3 domains of IgG4 is used as the template to generate the $Fc_{\gamma 4}$variant with Ser228Pro and Leu235Ala mutations ($vFc_{\gamma 4}$) in which Ser228 and Leu235 are replaced with Pro and Ala, respectively. The CH2 and CH3 regions is amplified using the 3' primer (SEQ ID NO:9) and a 5' primer containing the Leu235Ala mutation (SEQ ID NO:10). This amplified fragment, together with a synthetic oligonucleotide of 60 bases in length (SED ID NO:10) containing both Ser228Pro and Leu235Ala mutations, are joined in PCR by using SEQ ID NO:12 as the 5' primer and SEQ ID NO:9 as the 3' primer. The SEQ ID NO:12 primer contains sequences encoding a 16-amino acid Gly-Ser peptide linker including the BamHI site. The resulting DNA fragments of approximately 700 bp in length are inserted into a holding vector such as pUC19 at the BamHI and EcoRI sites to give the pL-vFcγ4 plasmid. The sequence of the gene is confirmed by DNA sequencing.

To prepare the hGH-L-$vFc_{\gamma 4}$fusion gene, the hGH fragment is excised from the phGH plasmid with HindIII and BamHI and then inserted to the 5'-end of the peptide linker in the pL-vFcγ4 plasmid to give the phGH-L-vFcγ4 plasmid. This fusion gene comprising hGH, a 16-amino acid Gly-Ser peptide linker and the $Fc_{\gamma 4}$ variant gene is then inserted at the HindIII and EcoRI sites of a mammalian expression vector, such as pcDNA3, as described for the hGH-L-$vFc_{\gamma 2}$ fusion protein. The final expression vector plasmid is designated as pGFP4. FIG. 2B shows a fusion gene containing sequences encoding hGH, a 16-amino acid peptide linker (GlySerGlyGlyGlySerGlyGlyGlyGlySerGlyGlyGlyGly Ser), and the $Fc_{\gamma 4}$ variant with Ser228Pro and Leu235Ala mutations.

3. Construction of the Gene Encoding the HuGH-L-$vFc_{\gamma 1}$ Fusion Protein

The hinge domain of human IgG1 heavy chain contains 15 amino acid residues (GluProLysSerCysAspLysThrHisThrCysProProCysPro) including 3 cysteine residues. Out of these 3 cysteine residues, the 2nd and 3rd are involved in the formation of disulfide bonding between two heavy chains. The 1st cysteine residue may pair with other cysteine residues, leading to nonspecific disulfide bonding. The hinge domain of $Fc_{\gamma 1}$ can be truncated to eliminate the 1st cysteine residue (AspLysThrHisThrCysProProCysPro). The gene encoding the $Fc_{\gamma 1}$ region is obtained by reverse transcription and PCR using RNA prepared from human leukocytes and appropriate 5' primer (SEQ ID NO:13) and 3' primer (SEQ ID NO:4). Resulting DNA fragments containing the truncated hinge and complete sequences of CH2 and CH3 domains of $Fc_{\gamma 1}$ is used as the template to generate the $Fc_{\gamma 1}$ variant with Leu234Val, Leu235Ala, and Pro331Ser mutations ($vFc_{\gamma 1}$).

One way to incorporate these mutations is as follows: two segments are produced and then assembled by using the natural $Fc_{\gamma 1}$ as the template in overlapping PCR. The 5' segment is generated by using SEQ ID NO:14 as the 5' primer and SEQ ID NO:5 as the 3' primer. This 5' primer contains the Leu234Val, Leu235Ala mutations and the 3' primer contains the Pro331Ser mutation. The 3' segment is generated by using SEQ ID NO:6 as the 5' primer and SEQ ID NO:4 as the 3' primer. These 5' and 3' segments are then joined at the region covering the Pro331Ser mutation by using SEQ ID NO:14 as the 5' primer and SEQ ID NO:4 as the 3' primer. This amplified fragment of approximately 650 bp in length, together with a synthetic oligonucleotide of 55 bases (SED ID NO:15) containing Leu234Val and Leu235Ala, are joined in PCR by using SEQ ID NO:16 as the 5' primer and SEQ ID NO:4 as the 3' primer. The SEQ ID NO:16 primer contains sequences encoding a 16-amino acid Gly-Ser peptide linker including the BamHI site. The resulting DNA fragments of approximately 700 bp in length are inserted into a holding vector such as pUC19 at the BamHI and EcoRI sites to give the pL-vFcγ1 plasmid. The sequence of the gene is confirmed by DNA sequencing.

To prepare the hGH-L-$vFc_{\gamma 1}$ fusion gene, the hGH fragment is excised from the phGH plasmid with HindIII and BamHI and inserted to the 5'-end of the peptide linker in the pL-vFcγ1 plasmid to give the phGH-L-vFcγ1 plasmid. The fusion gene comprising hGH, a 16-amino acid Gly-Ser peptide linker, and the $Fc_{\gamma 1}$ variant gene is then inserted at the HindIII and EcoRI sites of a mammalian expression vector, such as pcDNA3, as described for the hGH-L-$vFc_{\gamma 2}$ fusion protein. The final expression vector plasmid is designated as pGFP1. FIG. 2C shows a fusion gene containing sequences encoding hGH, a 16-amino acid peptide linker (GlySerGlyGlyGlySerGlyGlyGlyGlySerGlyGlyGlyGlySer), and the $Fc_{\gamma 1}$ variant with Leu234Val, Leu235Ala and Pro331Ser mutations.

4. Expression of the Fusion Protein in Transfected Cell Lines

The recombinant pGFP1, pGFP2 or pGFP4 expression vector plasmid is transfected into a mammalian host cell line to achieve the expression of the hGH-L-vFc fusion protein. For stable high levels of expression, a preferred host cell line is Chinese Hamster Ovary (CHO) cells deficient in the DHFR enzyme (see, for example, U.S. Pat. No. 4,818,679). A preferred method of transfection is electroporation. Other methods, including calcium phosphate co-precipitation, lipofectin, and protoplast fusion, can also be used. For electroporation, 10 μg of plasmid DNA linearized with BspCI is added to 2 to $5\times10^7$ cells in a cuvette using Gene Pulser Electroporator (Bio-Rad Laboratories, Hercules, Calif.) set at an electric field of 250 V and a capacitance of 960 μFd. Two days following the transfection, the media are replaced with growth media containing 0.8 mg/ml of G418. Transfectants resistant to the selection drug are tested for the secretion of the fusion protein by anti-human IgG Fc ELISA. Quantitation of the expressed fusion protein can also be carried out by ELISA using anti-hGH assays. The wells producing high levels of the Fc fusion protein are subcloned by limiting dilutions on 96-well tissue culture plates.

To achieve higher levels of the fusion protein expression, co-amplification is preferred by utilizing the gene of DHFR which can be inhibited by the MTX drug. In growth media containing increasing concentrations of MTX, the transfected fusion protein gene is co-amplified with the DHFR gene. Transfectants capable of growing in media with up to 1 μg/ml of MTX are again subcloned by limiting dilutions. The subcloned cell lines are further analyzed by measuring the secretion rates. Several cell lines yielding secretion rate levels over about 10 μg, preferably about 30 μg/$10^6$ [i.e. million] cells/24 h, are adapted to suspension culture using serum-free growth media. The conditioned media are then used for the purification of the fusion protein.

5. Purification and Characterization of the Fusion Protein

Conditioned media containing the fusion protein are titrated with 1 N NaOH to a pH of 7 to 8 and filtered through a 0.45 micron cellulose nitrate filter. The filtrate is loaded onto a Prosep A column equilibrated in phospate-buffered saline (PBS). After binding of the fusion protein to Prosep A, the flow-through fractions are discarded. The column is washed with PBS until OD at 280 nm is below 0.01. The bound fusion protein is then eluted with 0.1 M citrate buffer at pH 3.75. After neutralizing with 0.4 volume of 1 M $K_2HPO_4$, fractions containing purified protein are pooled and dialyzed against PBS. The solution is then filtered through a 0.22 micron cellulose nitrate filter and stored at 4° C. The molecular weight of purified hGH-L-vFc protein is in the range of 90 to 100 kDa by SDS-PAGE under non-reducing conditions. Under reducing conditions, the purified protein migrates around approximately 50 kDa. The fusion protein is quantitated by BCA protein assay using BSA as the standard.

6. In vitro Biological Potency Assays

Supernatants of transfectants or purified proteins can be tested for their ability to stimulate the proliferation of Nb2 rat lymphoma cells. Although Nb2 cells proliferate in response to hGH via the lactogenic receptors on the cells, the Nb2 cell bioassay can be a useful tool for evaluating the biological activity of hGH (for example, Uchida et al., *J. Mol. Endocrinol.* 23:347-353, 1999). Approximately 48 hours before the start of the assay, the cells are transferred to the pre-assay medium (Fisher's Medium supplemented with 1% horse serum, and 50 μM 2-ME) to slow down the rate of cell replication. After incubation, cells are collected and resuspended in assay medium (Fisher's Medium supplemented with 10% horse serum, and 50 μM 2-ME) at a concentration of $1\times10^5$ cells/ml. Two-hundred μl aliquots are distributed in each well of a 96-well microtiter plate. The plate is incubated in a $CO_2$ incubator (5% $CO_2$+95% air) for 48 hours at 37° C. To each well is added 50 μl culture supernatant containing various concentrations of the hGH-L-vFc fusion protein or rhGH control from 0.01 to 100 nM each. The plate is incubated in a $CO_2$ incubator for 48 h at 37° C. before 10 μl of MIT (3-[4, 5-dimethylthiazol-2-yl]-2,5-diphenyl-tetrazolium bromide) (2.5 mg/ml in PBS) is added to each well. After another 4 h in a $CO_2$ incubator at 37° C., the cells and formazan are solubilized by adding 100 μl per well of 10% SDS in 0.01 N HCl. The plate is then read at 550 nm with the reference beam set at 690 nm. The OD reading is plotted against the concentration of rhGH or the fusion protein. The biological activity of hGH-L-vFc relative to that of rhGH can therefore be compared quantitatively. The biological activity is good. A good activity for the present invention means an activity that is significant when comparing with, preferably the same as, and more preferably better than that of rhGH when measured on a molar basis.

Although the Nb2 cell bioassay can be a useful tool for evaluating the biological activity of hGH, cell proliferation depends on the cross reactivity of hGH with the lactogenic receptors on Nb2 cells. The Ba/F3-hGHR cell line, derived from mouse pro-B cell lymphoma cell line, is stably transfected with the hGHR gene and has been shown to express hGHR on cell surface. Cell proliferation assay using Ba/F3-hGHR cell line is mediated via the binding of hGH to hGHR on cell surface (For example, Ishikawa et al., *J. Clin. Endocrinol. & Metabol.* 85: 4274-4279, 2000). Approximately 4-6 hours before the start of the assays, the Ba/F3-hGHR cells are washed twice with assay medium (RPMI 1680, supplemented with 5% FCS, and 50 μM 2-ME) and are incubated in the assay medium for 4-6 h to slow down the rate of cell replication. After incubation, the cells are collected and resuspended at a concentration of $1\times10^5$ cells/ml. Two-hundred μl aliquots are distributed in each well of 96-well microtiter plate. To each well is added 50 μl culture supernatant containing various concentrations of the hGH-L-vFc fusion protein or recombinant hGH control from 0.01 to 100 nM each. The plate is incubated in a $CO_2$ incubator for 48 h at 37° C. At the end of the incubation, the colorimetric end point is determined as described above in the bioassay using the Nb2 cells. The biological activity is good. A good activity for the present invention means an activity that is significant when comparing with, preferably the same as, and more preferably better than that of rhGH when measured on a molar basis.

7. Pharmacokinetic Studies in Rats

Rats are divided into two groups to receive rhGH or purified hGH-L-vFc protein for a comparison of their plasma profiles. Female Sprague-Dawley rats (approximately 300 g) are administered a single s.c. injection of rhGH (100 μg/kg) or hGH-L-vFc (1 mg/kg) in PBS. In addition to pre-treatment sample, blood samples of 0.25 ml are collected in EDTA-coated micro tubes. Time points are collected at 1, 4, 8, 12, 24, 48, and 96 h after injection. Samples are stored on wet ice for up to 1 h prior to centrifugation and plasma harvest. Plasma samples are stored at −20° C. prior to analysis.

Concentration of hGH in plasma samples can be determined by using a commercial sandwich ELISA kit for detection of hGH (Invitrogen or Abnova). This kit detects hGH as well as hGH-L-vFc by means of an antibody sandwich ELISA format. Another ELISA format can also be used for the detection of hGH-L-vFc in rat plasma samples. In addition to using the anti-hGH antibody on the solid phase as included in the kit, anti-human IgG-heavy chain antibody is used in the antibody-enzyme (horseradish peroxidase) conjugate. By using the combination of anti-hGH and anti-human IgG-heavy chain detector antibodies, the ELISA measures specifically the concentration of hGH-L-vFc in plasma samples from the rats. The concentration of hGH is derived from a standard curve using materials supplied in the kit. The concentration of hGH-L-vFc is derived from a standard curve using hGH-L-vFc solutions ranging from 1 to 100 ng/ml (or approximately 0.01 to 1 nM).

The hGH-L-vFc or rhGH concentrations of serum samples are plotted against time points for the calculation of the circulation time. From these curves, standard pharmacokinetic parameters, including clearance (CL), half-life (t½), area under the plasma concentration versus time curve (AUC), and maximal observed plasma concentration ($C_{max}$) can be obtained. The concentration of hGH-L-vFc decreases much slower than that of rhGH, indicating longer half-life of the fusion protein in rats. It is within the scope of the present invention that a plasma half-life that is comparable to or equal to, preferably longer than [i.e. prolonged], and more preferably at least 2 times as long as that of rhGH when administered in vivo.

The examples described above are for illustration purposes only. They are not intended and should not be interpreted to limit either the scope or the spirit of this invention. It can be appreciated by those skilled in the art that many other variations or substitutes can be used as equivalents for the purposes of this invention, which is defined solely by the written description and the following claims.

TABLE 1

| Sequences of Oligonucleotides. |
|---|
| SEQ ID NO: 1 |
| 5'-cccaagcttggcgcggagatggctacaggctcccgga-3' |
| SEQ ID NO: 2 |
| 5'-cggatccgaagccacagctgccctcca-3' |
| SEQ ID NO: 3 |
| 5'-gtcgagtgcccaccgtgccca-3' |

TABLE 1-continued

| Sequences of Oligonucleotides. |
|---|
| SEQ ID NO: 4<br>5'-ggaattctcatttacccggagacaggga-3' |
| SEQ ID NO: 5<br>5'-tggttttctcgatggaggctgggaggcct-3' |
| SEQ ID NO: 6<br>5'-aggcctcccagcctccatcgagaaaacca-3' |
| SEQ ID NO: 7<br>5'-cggatccggtggcggttccggtggaggcggaagcggcggtgga ggatcagtcgagtgcccaccgtgccca-3' |
| SEQ ID NO: 8<br>5'-gagtccaaatatggtccccca-3' |
| SEQ ID NO: 9<br>5'-ggaattctcatttacccagagacaggga-3' |
| SEQ ID NO: 10<br>5'-cctgagttcgcgggggggacca-3' |
| SEQ ID NO: 11<br>5'-gagtccaaatatggtcccccatgcccaccatgcccagcacctg agttcgcgggggggacca-3' |
| SEQ ID NO: 12<br>5'-cggatccggtggcggttccggtggaggcggaagcggcggtgga ggatcagagtccaaatatggtccccca-3' |
| SEQ ID NO: 13<br>5'-gacaaaactcacacatgccca-3' |
| SEQ ID NO: 14<br>5'-acctgaagtcgcgggggggaccgt-3' |
| SEQ ID NO: 15<br>5'-gacaaaactcacacatgcccaccgtgcccagcacctgaagtcg cgggggggaccgt-3' |
| SEQ ID NO: 16<br>5'-cggatccggtggcggttccggtggaggcggaagcggcggtgga ggatcagacaaaactcacacatgccca-3' |

We claim:

1. A recombinant hGH-L-vFc fusion protein comprising hGH, a peptide linker, and a human IgG Fc variant, wherein the peptide linker containing about 20 or fewer amino acids is present between hGH and the human IgG Fc variant and wherein the human IgG Fc variant comprises a hinge, a CH2 domain, a CH3 domain of human IgG2, and serine residue at a position corresponding to residue 331 of SEQ ID NO:18.

2. The recombinant hGH-L-vFc fusion protein of claim 1 which exhibits a plasma half-life that is at least 2 times as long as that of rhGH (recombinant human growth hormone) when administered in vivo.

3. The recombinant hGH-L-vFc fusion protein of claim 1 wherein the peptide linker comprises two or more amino acids selected from the group consisting of glycine, serine, alanine, and threonine.

4. The hGH-L-vFc fusion protein of claim 3 which exhibits a plasma half-life that is at least 2 times as long as that of rhGH when administered in vivo.

* * * * *

SEQUENCE LISTING

<160> NUMBER OF SEQ ID NOS: 22

<210> SEQ ID NO 1
<211> LENGTH: 37
<212> TYPE: DNA
<213> ORGANISM: Artificial Sequence
<220> FEATURE:
<223> OTHER INFORMATION: PCR primer

<400> SEQUENCE: 1
cccaagcttg gcgcggagat ggctacaggc tcccgga 37

<210> SEQ ID NO 2
<211> LENGTH: 27
<212> TYPE: DNA
<213> ORGANISM: Artificial Sequence
<220> FEATURE:
<223> OTHER INFORMATION: PCR primer

<400> SEQUENCE: 2
cggatccgaa gccacagctg ccctcca 27

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
gtcgagtgcc caccgtgccc a 21

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
ggaattctca tttacccgga gacaggga 28

<210> SEQ ID NO 5
<211> LENGTH: 29
<212> TYPE: DNA
<213> ORGANISM: Artificial Sequence
<220> FEATURE:
<223> OTHER INFORMATION: PCR primer

<400> SEQUENCE: 5
tggttttctc gatggaggct gggaggcct 29

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
aggcctccca gcctccatcg agaaaacca 29

<210> SEQ ID NO 7
<211> LENGTH: 70
<212> TYPE: DNA
<213> ORGANISM: Artificial Sequence
<220> FEATURE:
<223> OTHER INFORMATION: PCR primer

<400> SEQUENCE: 7
cggatccggt ggcggttccg gtggaggcgg aagcggcggt ggaggatcag tcgagtgccc 60
accgtgccca 70

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
gagtccaaat atggtccccc a 21

<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
ggaattctca tttacccaga gacaggga 28

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
cctgagttcg cgggggacc a 21

<210> SEQ ID NO 11
<211> LENGTH: 60
<212> TYPE: DNA
<213> ORGANISM: Artificial Sequence
<220> FEATURE:
<223> OTHER INFORMATION: PCR primer

<400> SEQUENCE: 11
gagtccaaat atggtccccc atgcccacca tgcccagcac ctgagttcgc ggggggacca 60

<210> SEQ ID NO 12
<211> LENGTH: 70
<212> TYPE: DNA
<213> ORGANISM: Artificial Sequence
<220> FEATURE:
<223> OTHER INFORMATION: PCR primer

<400> SEQUENCE: 12
cggatccggt ggcggttccg gtggaggcgg aagcggcggt ggaggatcag agtccaaata 60
tggtccccca 70

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
gacaaaactc acacatgccc a 21

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
acctgaagtc gcggggggac cgt 23

<210> SEQ ID NO 15
<211> LENGTH: 55
<212> TYPE: DNA
<213> ORGANISM: Artificial Sequence
<220> FEATURE:
<223> OTHER INFORMATION: PCR primer

<400> SEQUENCE: 15
gacaaaactc acacatgccc accgtgccca gcacctgaag tcgcgggggg accgt 55

<210> SEQ ID NO 16
<211> LENGTH: 70
<212> TYPE: DNA
<213> ORGANISM: Artificial Sequence
<220> FEATURE:
<223> OTHER INFORMATION: PCR primer

<400> SEQUENCE: 16
cggatccggt ggcggttccg gtggaggcgg aagcggcggt ggaggatcag acaaaactca 60
cacatgccca 70

<210> SEQ ID NO 17
<211> LENGTH: 1392
<212> TYPE: DNA
<213> ORGANISM: Artificial Sequence
<220> FEATURE:
<223> OTHER INFORMATION: hGH-L-vFc gamma2 (Figure 2A)

<400> SEQUENCE: 17

```
aagcttctag ctgcaatggc tacaggctcc cggacgtccc tgctcctggc ttttggcctg     60
ctctgcctgc cctggcttca agagggcagt gccttcccaa ccattccctt atccaggctt    120
tttgacaacg ctatgctccg cgcccatcgt ctgcaccagc tggcctttga cacctaccag    180
gagtttgaag aagcctatat cccaaaggaa cagaagtatt cattcctgca gaacccccag    240
acctccctct gtttctcaga gtctattccg acaccctcca acagggagga aacacaacag    300
aaatccaacc tagagctgct ccgcatctcc ctgctgctca tccagtcgtg gctggagccc    360
gtgcagttcc tcaggagtgt cttcgccaac agcctggtgt acggcgcctc tgacagcaac    420
gtctatgacc tcctaaagga cctagaggaa ggcatccaaa cgctgatggg gaggctggaa    480
gatggcagcc cccggactgg gcagatcttc aagcagacct acagcaagtt cgacacaaac    540
tcacacaacg atgacgcact actcaagaac tacgggctgc tctactgctt caggaaggac    600
atggacaagg tcgagacatt cctgcgcatc gtgcagtgcc gctctgtgga gggcagctgt    660
ggcttcggat ccggtggcgg ttccggtgga ggcggaagcg gcggtggagg atcagtcgag    720
tgcccaccgt gcccagcacc acctgtggca ggaccgtcag tcttcctctt ccccccaaaa    780
cccaaggaca ccctcatgat ctcccggacc cctgaggtca cgtgcgtggt ggtggacgtg    840
agccacgaag accccgaggt ccagttcaac tggtacgtgg acggcgtgga ggtgcataat    900
gccaagacaa agccacggga ggagcagttc aacagcacgt tccgtgtggt cagcgtcctc    960
accgttgtgc accaggactg gctgaacggc aaggagtaca agtgcaaggt ctccaacaaa   1020
ggcctcccag cctccatcga gaaaaccatc tccaaaacca aagggcagcc ccgagaacca   1080
caggtgtaca ccctgccccc atcccgggag gagatgacca agaaccaggt cagcctgacc   1140
tgcctggtca aaggcttcta ccccagcgac atcgccgtgg agtgggagag caatgggcag   1200
ccggagaaca actacaagac cacacctccc atgctggact ccgacggctc cttcttcctc   1260
tacagcaagc tcaccgtgga caagagcagg tggcagcagg ggaacgtctt ctcatgctcc   1320
gtgatgcatg aggctctgca caaccactac acgcagaaga gcctctccct gtctccgggt   1380
aaatgagaat tc                                                       1392
```

<210> SEQ ID NO 18
<211> LENGTH: 456
<212> TYPE: PRT
<213> ORGANISM: Artificial Sequence
<220> FEATURE:
<223> OTHER INFORMATION: hGH-L-Fc gamma2 with a 26-amino acid leader peptide (Figure 2A)

<400> SEQUENCE: 18

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95
```

```
Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Ser Gly Gly Gly Ser Gly
    210                 215                 220

Gly Gly Gly Ser Gly Gly Gly Gly Ser Val Glu Cys Pro Pro Cys Pro
225                 230                 235                 240

Ala Pro Pro Val Ala Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Phe Arg Val Val Ser Val Leu Thr Val Val His Gln
305                 310                 315                 320

Asp Trp Leu Asn Gly Lys Glu Tyr Lys Cys Lys Val Ser Asn Lys Gly
                325                 330                 335

Leu Pro Ala Ser Ile Glu Lys Thr Ile Ser Lys Thr Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Met Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

<210> SEQ ID NO 19
<211> LENGTH: 1410
<212> TYPE: DNA
<213> ORGANISM: Artificial Sequence
<220> FEATURE:
<223> OTHER INFORMATION: hGH-L-vFc gamma4 (Figure 2B)

<400> SEQUENCE: 19

```
aagcttctag ctgcaatggc tacaggctcc cggacgtccc tgctcctggc ttttggcctg     60
ctctgcctgc cctggcttca agagggcagt gccttcccaa ccattccctt atccaggctt    120
tttgacaacg ctatgctccg cgcccatcgt ctgcaccagc tggcctttga cacctaccag    180
gagtttgaag aagcctatat cccaaaggaa cagaagtatt cattcctgca gaacccccag    240
acctccctct gtttctcaga gtctattccg acaccctcca acagggagga aacacaacag    300
aaatccaacc tagagctgct ccgcatctcc ctgctgctca tccagtcgtg gctggagccc    360
gtgcagttcc tcaggagtgt cttcgccaac agcctggtgt acggcgcctc tgacagcaac    420
gtctatgacc tcctaaagga cctagaggaa ggcatccaaa cgctgatggg gaggctggaa    480
gatggcagcc cccggactgg gcagatcttc aagcagacct acagcaagtt cgacacaaac    540
tcacacaacg atgacgcact actcaagaac tacgggctgc tctactgctt caggaaggac    600
atggacaagg tcgagacatt cctgcgcatc gtgcagtgcc gctctgtgga gggcagctgt    660
ggcttcggat ccggtggcgg ttccggtgga ggcggaagcg gcggtggagg atcagagtcc    720
aaatatggtc ccccatgccc accatgccca gcacctgagt tcgcgggggg accatcagtc    780
ttcctgttcc ccccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa   1080
gggcagcccc gagagccaca ggtgtacacc ctgcccccat cccaggagga gatgaccaag   1140
aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca agagcaggtg gcaggagggg   1320
aatgtcttct catgctccgt gatgcatgag gctctgcaca accactacac acagaagagc   1380
ctctccctgt ctctgggtaa atgagaattc                                    1410
```

<210> SEQ ID NO 20
<211> LENGTH: 462
<212> TYPE: PRT
<213> ORGANISM: Artificial Sequence
<220> FEATURE:
<223> OTHER INFORMATION: hGH-L-vFc gamma4 with a 26-amino acid leader peptide (Figure 2B)

<400> SEQUENCE: 20

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95
```

```
Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Ser Gly Gly Gly Ser Gly
    210                 215                 220

Gly Gly Gly Ser Gly Gly Gly Gly Ser Glu Ser Lys Tyr Gly Pro Pro
225                 230                 235                 240

Cys Pro Pro Cys Pro Ala Pro Glu Phe Ala Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460


<210> SEQ ID NO 21
<211> LENGTH: 1404
<212> TYPE: DNA
<213> ORGANISM: Artificial Sequence
<220> FEATURE:
<223> OTHER INFORMATION: hGH-L-vFc gamma1 (Figure 2C)
```

<400> SEQUENCE: 21

```
aagcttctag ctgcaatggc tacaggctcc cggacgtccc tgctcctggc ttttggcctg     60

ctctgcctgc cctggcttca agagggcagt gccttcccaa ccattccctt atccaggctt    120

tttgacaacg ctatgctccg cgcccatcgt ctgcaccagc tggcctttga cacctaccag    180

gagtttgaag aagcctatat cccaaaggaa cagaagtatt cattcctgca gaacccccag    240

acctccctct gtttctcaga gtctattccg acaccctcca acagggagga aacacaacag    300

aaatccaacc tagagctgct ccgcatctcc ctgctgctca tccagtcgtg gctggagccc    360

gtgcagttcc tcaggagtgt cttcgccaac agcctggtgt acggcgcctc tgacagcaac    420

gtctatgacc tcctaaagga cctagaggaa ggcatccaaa cgctgatggg gaggctggaa    480

gatggcagcc cccggactgg gcagatcttc aagcagacct acagcaagtt cgacacaaac    540

tcacacaacg atgacgcact actcaagaac tacgggctgc tctactgctt caggaaggac    600

atggacaagg tcgagacatt cctgcgcatc gtgcagtgcc gctctgtgga gggcagctgt    660

ggcttcggat ccggtggcgg ttccggtgga ggcggaagcg gcggtggagg atcagacaaa    720

actcacacat gcccaccgtg cccagcacct gaagtcgcgg ggggaccgtc agtcttcctc    780

ttccccccaa aacccaagga caccctcatg atctcccgga cacctgaggt cacatgcgtg    840

gtggtggacg tgagccacga agaccctgag gtcaagttca actggtacgt ggacggcgtg    900

gaggtgcata atgccaagac aaagccgcgg gaggagcagt acaacagcac gtaccgggtg    960

gtcagcgtcc tcaccgtcct gcaccaggac tggctgaatg gcaaggagta caagtgcaag   1020

gtctccaaca aagccctccc agcctccatc gagaaaacca tctccaaagc caaagggcag   1080

ccccgagaac cacaggtgta caccctgccc ccatcccggg atgagctgac caagaaccag   1140

gtcagcctga cctgcctggt caaaggcttc tatcccagcg acatcgccgt ggagtgggag   1200

agcaatgggc agccggagaa caactacaag accacgcctc ccgtgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaatgaga attc                                          1404
```

<210> SEQ ID NO 22
<211> LENGTH: 460
<212> TYPE: PRT
<213> ORGANISM: Artificial Sequence
<220> FEATURE:
<223> OTHER INFORMATION: hGH-L-vFc gamma1 with a 26-amino acid leader peptide (Figure 2C)

<400> SEQUENCE: 22

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95
```

-continued

```
Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Ser Gly Gly Gly Ser Gly
    210                 215                 220

Gly Gly Gly Ser Gly Gly Gly Gly Ser Asp Lys Thr His Thr Cys Pro
225                 230                 235                 240

Pro Cys Pro Ala Pro Glu Val Ala Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Ser Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```